United States Patent [19]

Moody et al.

[11] Patent Number: 4,999,446

[45] Date of Patent: Mar. 12, 1991

[54] TRIMETHOXYSILANE PREPARATION VIA THE METHANOL-SILICON REACTION WITH RECYCLE

[75] Inventors: Lawrence G. Moody, Marietta; Thomas E. Childress, Newport, both of Ohio; Robert L. Pitrolo, Parkersburg, W. Va.; James S. Ritscher; Ronald P. Leichliter, both of Marietta, Ohio

[73] Assignee: Union Carbide Chemicals and Plastics Company Inc., Danbury, Conn.

[21] Appl. No.: 541,516

[22] Filed: Jun. 21, 1990

[51] Int. Cl.$^5$ ............................................. C07F 7/04
[52] U.S. Cl. ..................................................... 556/470
[58] Field of Search .......................................... 556/470

[56] References Cited

U.S. PATENT DOCUMENTS

| 2,473,260 | 6/1949 | Rechew | 260/448.8 |
| 3,072,700 | 2/1963 | de Wit | 260/448.8 |
| 3,775,457 | 11/1973 | Marseka et al. | 556/470 |
| 4,288,604 | 9/1981 | Magee et al. | 556/470 |
| 4,447,632 | 5/1984 | Mallon | 556/470 |
| 4,487,949 | 12/1984 | Mallon | 556/470 |
| 4,727,173 | 2/1988 | Mendicino | 556/470 |
| 4,761,492 | 8/1988 | Childress et al. | 556/482 |
| 4,762,939 | 8/1988 | Mendicino | 556/470 |
| 4,931,578 | 6/1990 | Ohta et al. | 556/470 |

FOREIGN PATENT DOCUMENTS

| 163529 | 6/1979 | Japan | 556/470 |
| 11538 | 1/1980 | Japan | 556/470 |
| 0001694 | 7/1986 | Japan | 556/470 |
| 0027993 | 5/1988 | Japan | 556/470 |

*Primary Examiner*—Paul F. Shaver
*Attorney, Agent, or Firm*—Bonnie L. Deppenbrock

[57] ABSTRACT

A process for producing trimethoxysilane by reacting methanol and silicon metal in the presence of a copper catalyst, and optionally an inert solvent, in which the trimethoxysilane-methanol azeotrope is recycled, characterized by maintaining a 60% methanol conversion.

38 Claims, 1 Drawing Sheet

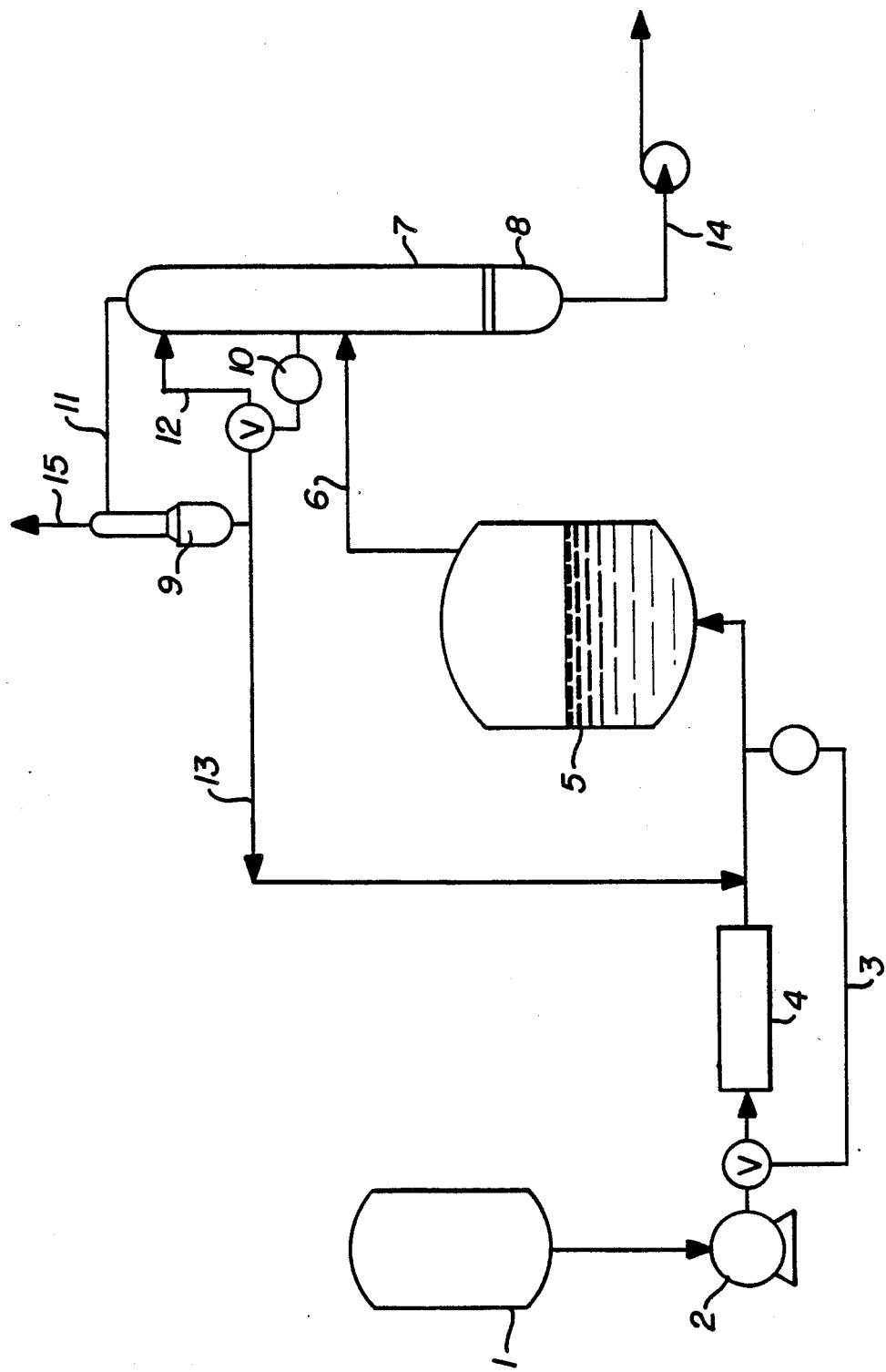

TRIMETHOXYSILANE PREPARATION VIA THE METHANOL-SILICON REACTION WITH RECYCLE

BACKGROUND OF THE INVENTION

1. Field of the Invention

The present invention relates to a process for converting silicon metal and methanol to trimethoxysilane and in particular to a process in which a mixture containing trimethoxysilane and methanol (in the azeotropic ratio of 55% trimethoxysilane to 45% methanol by weight) is recycled to a reactor without employing a separate azeotropic or extractive distillation step.

2. Prior Art

The reaction between silicon metal and alcohol to produce alkoxysilanes and silicates is well established. As early as 1949, U.S. Pat. No. 2,473,260 described a process for the preparation of methyl silicates from methanol and silicon-copper masses. Subsequently, U.S. Pat. No. 3,072,700 taught the preparation of alkoxysilanes from silicon metal and alcohol in a fluidized bed reactor.

Patents on the production of tetraalkylorthosilicates include U.S. Pat. No. 4,288,604 and Japanese Pat. No. 1979-163529. A patent covering the production of trialkoxysilanes is U.S. Pat. No. 3,775,457. One of the problems associated with such processes is the difficulty of removing the unreacted alcohol from the desired silane.

In Japanese Laid Open Application No. 1980-11538 is described a process to produce trimethoxysilane wherein the unreacted methanol in the product is removed by breaking the trimethoxysilane-methanol azeotrope by adding a third component, e.g., hexane, in an amount proportional to the amount of methanol present and then distilling to remove the methanol as the hexane-methanol azeotrope.

U.S Pat. No. 4,761,492, discloses a process in which methanol is separated from crude product containing trimethoxysilane using extractive distillation with tetramethoxysilane as the solvent. This process requires a relatively large quantity of tetramethoxysilane for extractive distillation. That is, the ratio of tetramethoxysilane to the crude product must be equal to or greater than 2:1. This requirement means that the extraction column must handle a flowrate of at least three times the desired production rate of the crude product. Therefore, the column diameter and number of trays (approximately 50 to 60) are in excess of what would otherwise be needed for the extraction column. Another problem with the process is the difficulty of obtaining high purity trimethoxysilane (i.e., greater than 99%) given the large ratio of tetramethoxysilane. Because of this ratio, separation of high purity trimethoxysilane is difficult to achieve even in a second distillation column.

It is known in the art that when methanol and silicon metal are reacted to make trimethoxysilane, large quantities of unreacted methanol are generally present in the reactor product. While the industry has long desired and felt that there was a need to recycle unreacted methanol to the reactor for economic reasons, it was generally believed not to be possible or feasible without separation of the methanol from a crude product. It has been generally taught in the art that removal of this unreacted methanol is required prior to utilizing the trimethoxysilane in order to avoid the reaction of methanol with trimethoxysilane to form hydrogen and tetramethoxysilane. For example, in U.S. Pat. No. 4,727,173 (Column 3, lines 48-51), it is stated, "If the crude product is recycled to the reactor with the trimethoxysilane unremoved, the trimethoxysilane will likely react further with the methanol to produce tetramethoxysilane." And further, Japanese Laid Open Application No. 1980-11538 (page 5, lines 12) states "it is necessary to separate and remove unreacted methanol rapidly from the reaction mixture in order to obtain methoxysilane, particularly trimethoxysilane, at a high yield." Therefore, the manufacture of trimethoxysilane from silicon metal and methanol required extractive distillation; or, alternatively, subsequent, separate azeotropic distillation using a third component, such as hexane, to break the azeotrope.

It is well known in the art that methanol and trimethoxysilane form a relatively low boiling (i.e., a normal boiling point of about 62.5° C.) azeotrope which is about 55 wt % trimethoxysilane and 45 wt % methanol. Similarly, methanol has a normal boiling point of about 64.5° C., while trimethoxysilane has a normal boiling point of about 84° C. Since the azeotrope has the lowest boiling point, it is not possible to separate a stream containing methanol and trimethoxysilane into a stream of pure methanol and a stream of a pure trimethoxysilane by simple distillation alone.

Because methanol and trimethoxysilane form a low boiling azeotrope which is about 55 wt % trimethoxysilane and 45 wt % methanol, and methanol and trimethoxysilane react at elevated temperatures, it was believed that "azeotrope recycle" would result in large trimethoxysilane losses and poor selectivity. Selectivity here refers to the amount of trimethoxysilane relative to the amount of tetramethoxysilane contained in the reactor product. Further, it was believed even if azeotrope recycle were to be attempted, the volume of the recycle feed would be so large that the equipment required for handling would be costly and unwieldy. Also, effectively handling such volume would raise concerns about safety and controlability of the process. Until the present invention, recycle has been impractical and unknown.

Accordingly, a need continues to exist for a commercially attractive process to recover trimethoxysilane relatively free from methanol and tetramethoxysilane.

OBJECTIVES OF THE INVENTION

It is a primary object of the present invention to provide a process for producing trimethoxysilane which eliminates the need for a separate or subsequent extractive distillation step, and at the same time does not require the addition of a third component to break the trimethoxysilane-methanol azeotrope.

Another object of the present invention is that such a process be capable of being run at high temperatures with acceptable raw material to trimethoxysilane efficiencies.

Still another object of the present invention is to provide improved control in a continuous process for production of trimethoxysilane.

Another object of the present invention is to eliminate the need for storage (prior to any subsequent and further purification or refining) of a crude trimethoxysilane product containing significant quantities of methanol.

A further object of the present invention is to reduce the quantity of tetramethoxysilane used in the process as compared to the quantity used in an extractive distillation with tetramethoxysilane.

Other objects and advantages of the present invention will be made apparent by the description and examples which follow.

SUMMARY OF THE INVENTION

The present invention provides a process for producing trimethoxysilane by introducing methanol into a reactor containing silicon metal and an effective amount of a copper catalyst which is maintained at a temperature of at least 180° C. The temperature and mixing conditions in the reactor are controlled so that the percent methanol conversion is at least 60% to form a reactor product containing trimethoxysilane-methanol azeotrope and trimethoxysilane. The reactor product is fed into a distillation column, where it is distilled into a lites stream containing a trimethoxysilane-methanol azeotrope and a heavies stream containing trimethoxysilane and small amounts of tetramethoxysilane. The lites stream is subsequently recycled to the reactor. Trimethoxysilane is removed in the heavies stream.

BRIEF DESCRIPTION OF THE DRAWING

FIG. 1 illustrates schematically the material flow and operational steps which can be employed in one embodiment of the process of the present invention.

DETAILED DESCRIPTION OF THE DRAWING

The FIG. 1 is a schematic illustration of a process for producing trimethoxysilane via the methanol-silicon reaction with recycle of the lites stream containing the trimethoxysilane-methanol azeotrope.

From a methanol feed tank (1), methanol is fed to a pump (2) having a flow control means (3). and optionally via a vaporizer (4) to the reactor (5) In the reactor, the methanol reacts with the silicon in the presence of an effective amount of copper catalyst to produce a gaseous reactor product (6) consisting of unreacted methanol, trimethoxysilane (which, thus, includes a trimethoxysilane-methanol azeotrope), a small amount of tetramethoxysilane and trace amounts of dimethoxysilane and disiloxanes. The reactor product is fed to a distillation column (7) equipped with a reboiler (8), a reflux condenser (shown as external) (9) and temperature control means (10). The column temperature is controlled such that the azeotrope (and, thus, the unreacted methanol) is taken overhead in a lites stream (11). A portion of the lites stream (12) is returned to the column (7) in order to maintain reflux. The remainder of the overhead or lites stream (13) is recycled to the reactor. The remaining trimethoxysilane and small amounts of tetramethoxysilane in the column (7) are recovered as final product in a heavies stream (14). Hydrogen produced in the reaction is vented via the reflux condenser (9) and is depicted as stream (15).

The heavies stream (14) may be removed and stored to allow accumulation of material prior to further distillation. In contrast to other methods known in the art, the heavies stream is substantially free of methanol and, consequently, the trimethoxysilane reaction with methanol which liberates hydrogen and heat does not occur.

DETAILED DESCRIPTION OF THE INVENTION

In accordance with the present invention there is provided a process for producing trimethoxysilane as follows:

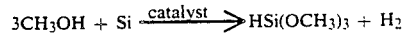

Trimethoxysilane is produced by the reaction of methanol and silicon metal in the presence of a copper catalyst to produce a reactor product containing a mixture of unreacted methanol, trimethoxysilane, and, thus, the azeotrope. Thereafter, the reactor product is distilled, generating a lites stream containing the azeotrope and, thus, unreacted methanol, which is recycled to the reactor and a heavies stream, containing trimethoxysilane, small amounts of tetramethoxysilane, and disiloxanes, which is removed and may be further distilled, if desired, to yield high purity trimethoxysilane. The hydrogen produced in the reaction is released.

Silicon

The silicon metal used in the process of this invention can generally be any commercially available grade of silicon in particulate form. A typical composition of commercial silicon metal useful in this invention, expressed in percent by weight, is silicon-98.5%; iron-less than 0.50%; aluminum-0.20 to 0.35%; calcium-0.02 to 0.10%; water-less than 0.1%; lead-less than 10 ppm; boron-less than 20 ppm. Generally smaller particle size (less than about 420 microns) is preferred for ease of processing. Most preferably the particle size ranges from about 75 to 300 microns. Sieving of ground silicon to regulate particle size is optional. Silicon and an effective amount of catalyst can be added batchwise or semi-continuously during the process of the present invention.

The presence of tin in the reaction involved in the process of the present invention has adverse effects on the reaction rate and so whenever possible should be avoided (e.g., amounts as low as 75 parts per million have been shown to have an adverse effect on the reaction).

Methanol

The only alcohol useful in the process of the present invention is methanol ($CH_3OH$). Other alcohols do not work in the present invention because they do not form an azeotrope with their respective trialkoxysilane. The amount of methanol employed is at least a stoichiometric amount based on the amount of silicon metal used. Any unreacted methanol is recycled. Methanol may be introduced into the reactor as a gas or a liquid. However, it is preferred to introduce methanol as a gas.

Catalyst

The catalyst used in the process of this invention is present in the reactor in an amount effective to catalyze the reaction of the methanol and silicon to form trimethoxysilane. Generally an effective amount ranges from about 0.01 to about 5 parts by weight of catalyst per 100 parts by weight of the silicon metal. Usually the amount of catalyst will be from about 0.1 to about 2.6 parts by weight per 100 parts by weight of the silicon metal. The preferred amount of catalyst is from about 0.1 to about 0.7 parts by weight per 100 parts by weight of silicon metal.

The preferred catalysts employed in the process of the present invention are selected from the group consisting of powdered metallic copper, any anhydrous copper compounds, and mixtures thereof.

Examples of anhydrous copper compounds particularly suitable for use alone or in mixtures are the copper oxides, e.g. cupric oxide and cuprous oxide; copper halides, e.g. cupric chloride, cuprous chloride, cuprous bromide, cupric bromide; copper nitrates; copper salts of lower aliphatic acids such as cupric formate and cupric acetate; copper carbonates; copper hydroxides; copper cyanides; intermetallic copper compounds such as lead-free bronzes and brasses; and copper acetylacetonate. This, however, is not a restrictive or exclusive list. Preferred catalysts include cupric oxide, cuprous oxide, cupric chloride, copper hydroxides and their mixtures. Most preferably, stabilized copper (II) hydroxide is employed. Stabilized copper hydroxide may be purchased for Alfa Products, Don Ingram Company, Inc., and Kocide Chemical Corporation.

Copper compounds specifically to be avoided as catalysts in the present process are those such as copper phosphide, copper sulfides and inter-metallic compounds of lead and copper.

Metallic silver, its compounds such as silver oxide and silver chloride, and their mixtures are also known to be effective catalysts but are not considered optimum for the present process.

Solvent

The process of the present invention may utilize a solvent to disperse the silicon in a fluid state (slurry), although one is not necessary. In the preferred embodiment of the present invention a solvent is utilized. Solvents useful in the process of the present invention are inert, that is, a solvent that does not substantially (or significantly) degrade under the reaction conditions of the process. Generally, the inert solvent employed in the present invention is a high temperature stable organic solvent. Suitable inert solvents that may be employed include paraffinic hydrocarbons (e.g., dodecane); polyalkylated aromatic hydrocarbons (e.g. THERMINOL TM 59, THERMINOL TM 60, THERMINOL TM 66,); and mixtures thereof. Polyalkylated aromatic hydrocarbons and mixtures thereof are the preferred solvents for use in the present invention. The most preferred solvent is THERMINOL TM 59. (Note THERMINOL TM is the Monsanto Company tradename for heat transfer fluids having thermal stability and low vapor pressure, i.e., not higher than about 170 Torr at 250° C.)

The amount of solvent employed is a function of the amount of silicon metal present. Generally, from one part of solvent per two parts of silicon metal (1:2) to four parts of solvent per one part of silicon metal (4:1) will be required. Preferably this ratio will range from 1:1 to 2:1.

Reactor

A wide variety of reactor designs are suitable for use in the present invention. Any reactor in which the silicon metal and catalyst can be contacted with methanol at reaction temperatures of at least 180° C. may be employed. When the process of the present invention does not employ a solvent, the reaction is a two phase, gas-solid system. Reactors useful when no solvent is used in the process of the present invention include, but are not limited to, fluidized bed, fixed bed, and moving bed. When the process of the present invention does utilize a solvent, the reaction is a three phase, gas-liquid-solid system. Reactors useful when a solvent is employed in the present invention include, but are not limited to a slurry reactor (three phase fluidized bed), mechanically agitated tank and trickle bed. A single reactor or multiple reactors may be employed. When multiple reactors are employed, the reactors may be the same or different. For example, a stirred reactor, a fluidized bed reactor and a packed bed reactor may be used in sequence.

Reactor Product

In the process of the present invention the reactor product contains hydrogen, methanol, trimethoxysilane, and, thus, the trimethoxysilane-methanol azeotrope, a small amount of tetramethoxysilane, and trace amounts of dimethoxysilane and disiloxanes. The reactor product may be gaseous or liquid depending on the pressures and temperatures utilized. Preferably the reactor product is substantially gaseous.

Distillation Column

Any means for separating the reactor product into a lites stream and a heavies stream may be employed in the process of the present invention. Typically a distillation column is employed in the process of the present invention. The column may be a standard single stage column or a multi-stage column. The column may contain trays or packing. A multi-stage distillation column is generally preferred in order to separate trimethoxysilane-methanol azeotrope, that is in the lites stream which is recycled to the reactor from the trimethoxysilane product that is in the heavies stream. Preferably the reactor and column are close coupled and the lites stream is immediately and/or continuously recycled to the reactor. However, storage may be provided for the reactor product before separation by a column or for the lites after separation and before re-entry into the reactor. Storage for these two streams, however, is not preferred because of the reaction of trimethoxysilane with methanol to form tetramethoxysilane. As mentioned, storage of the heavies stream is acceptable because it is essentially methanol free, so that the formation of tetramethoxysilane by reaction of trimethoxysilane with methanol does not occur to any significant degree. Start up can be conducted with or without the column in operation. Generally, better results were obtained when the column was started with the reactor.

Separating the reactor product in the distillation column can be accomplished by a number of methods known in the art. For example, a sensor can be used to measure one or more physical parameters (e.g. temperature, differential pressure, density, refractive index), or other quantifiable property that differentiates the lites stream from the heavies stream. Output from the sensor is compared to a preset, desired value for a selected parameter, and the degree of deviation from that value is used to regulate a control means (e.g. a valve or rheostat) that in turn regulates one or more operating variables associated with the column. Such variables known to those skilled in the art can be, for example, (i) heat input to a reboiler or boil-up rate, (ii) return flow of condensed lites to the column or reflux ratio. In a preferred embodiment, temperature is measured by a sensor, and regulates the flow rate of condensed lites stream being returned to the column to provide reflux to control separation of the two streams in the column. Differential pressure is sensed by another sensor and regulates the heat input to the reboiler thereby ensuring a sufficient quantity of trimethoxysilane in the column to allow control of the separation of the two streams by the above-described reflux.

Lites

The lites stream is the recycle stream flowing from the distillation column to the reactor. The lites stream contains mainly trimethoxysilane-methanol azeotrope with small amounts of dimethoxysilane. Lites may be recycled to the reactor as gas or liquid. In the present invention the azeotrope is recycled to the reactor where the methanol in the azeotrope is again contacted with the silicon metal to produce more of the desired trimethoxysilane. The small amount of dimethoxysilane in the lites stream reacts with methanol to form the desired product, trimethoxysilane. Preferably, the lites stream is substantially in vapor form and is recycled directly to the reactor. That is, the lites stream is preferably not condensed, stored, or heated prior to entering the reactor. The lites stream flows out of the upper portion or top of the column. That is, the lites stream is the "overhead" stream of the column.

Heavies

The heavies stream is the stream containing the greater concentration of trimethoxysilane product and it flows from the lower portion or bottom of the distillation column. The heavies stream contains trimethoxysilane and small amounts of tetramethoxysilane. If desired, the heavies stream may be further refined or purified by a second distillation step or stored. Because no components are present which form an azeotrope with trimethoxysilane, additional refinement, if desired, may be accomplished using simple distillation (as opposed to extractive distillation or using a third component to break the azeotrope). However, for many subsequent applications using trimethoxysilane this additional refinement is not required.

% Methanol Conversion

In accordance with the present invention, recycle may be effectively and efficiently accomplished if the lites stream containing the azeotrope is immediately recycled without storage or substantial delay. Also, the process of the present invention must be carried out such that the methanol conversion in the reactor as measured in the reactor product from the reactor is equal to or greater than about 60%. Less than 60% methanol conversion results in more methanol in the reactor product than can be recycled as the azeotrope. That is, in the present invention, methanol is recycled "as" or "in" the azeotrope.

In general, the higher methanol conversion in the reactor, the lower the amount of lites for recycle. In the present invention higher methanol conversions generally lead to selectivities of trimethoxysilane comparable to processes utilizing subsequent extractive distillation or third component (e.g., hexane) breaking of the azeotrope. While the minimum theoretical % methanol conversion required in the process of the present invention is about 60%, the preferred % methanol conversion is equal to or greater than about 70%, and most preferably greater than about 80%.

Percent methanol conversion is measured by the following equation:

$$\% \text{ MeOH Conversion} = \frac{\text{lbs. of MeOH reacted (in reactor product)}}{\text{lbs. of MeOH fed into the reactor}} \times 100$$

A number of factors affect the % methanol conversion, but are not critical to, the process of the present invention. Optimization of these factors for the desired % methanol conversion is readily accomplished. For example, the % methanol conversion increases as the methanol feed rate decreases. For a mechanically agitated slurry reactor, methanol feed rates less than about $$1.5 \frac{\text{pounds of MeOH/hr}}{\text{pounds silicon in the reactor}}$$

will result in acceptable % methanol conversions. Other types of reactors require different optimization. At the beginning and end of the process, when silicon metal reactivity is low, much smaller methanol feed rates are required for good methanol conversion. Different raw materials and reactor conditions may affect the methanol feed rate.

Percent methanol conversion increases as reactor pressure increases. However, there are disadvantages in operating both below or above atmospheric pressure. Operation below atmospheric pressure increases the risk of explosion due to air leakage in the system. Operation above atmospheric pressure increases the risk of a leak to the environment.

When an inert solvent is used in the process of the present invention, the % methanol conversion depends on the rate of mass transfer of methanol from the gas phase to the slurry phase. In general, the faster the rate of mass transfer, the higher the % methanol conversion. For a mechanically agitated reactor, two criteria are important for achieving an acceptable rate of mass transfer:

1. the turbine RPM must be at or above the gas/liquid flooding point; and
2. the turbine RPM must be at or above the minimum for silicon particle suspension.

For example, for the 6-inch diameter reactor used in the examples, the minimum RPM of the 2.5 inch diameter turbine was about 500 RPM. Different reactor/turbine sizes may require different RPM's to achieve comparable rates of mass transfer.

Percent methanol conversion increases as reaction temperature increases. However, too high a temperature may lead to poor silicon metal conversion. A temperature of about 250° C. is the optimum temperature for the process of the present invention. And, in general, % methanol conversion increases as catalyst loading increases. Also, as the silicon metal particle size decreases, the % methanol increases.

Other advantages believed to exist from operating at a % methanol conversion of equal to or greater than 60% are further simplicity of the process in that only one reactor is needed; extractive distillation or azeotropic breaking by a third component is no longer necessary; and the distillation apparatus is smaller and easier to control.

Reaction Conditions

In the process of the present invention the silicon metal, catalyst and preferably a solvent can be added to the reactor in any order. Generally, the reaction is run in a slurry of silicon metal, catalyst and solvent, and the methanol is introduced into the slurry as a gas or liquid at a fixed rate. The reaction typically displays a one or two hour induction period. The initial methanol feed rate is therefore low and is brought up as the reaction progresses. Generally, once the reaction is running, the methanol feed rate can be adjusted to give the desired level of methanol conversion. The desired conversion can be maintained by a flow control means on the methanol feed. The flow control means is utilized to control, via a control valve, the total flow to the reaction by varying the quantity of "make-up" or fresh methanol entering the reactor. One skilled in the art can also readily adjust the feed rate in a given reaction run by monitoring the composition of the reactor product. If the feed rate is too high, the reactor product stream will contain a larger proportion of unreacted methanol.

The reaction is generally conducted at temperatures above about 180° C but below such a temperature that would degrade or decompose the reactants or solvents. Preferably the reaction temperature is maintained in a range from about 200° C. to about 280° C. Most preferably the reaction temperature is about 240° to 280° C. The reaction could of course be run at higher temperatures although at no particular advantage. In the column, the desired lites separation can be controlled by a temperature control means, such as a thermocouple, located on the distillation column and attached to a control valve in a reflux flow line to the column. By regulating the reflux flow to the column via a valve and the temperature in the upper portion of the column and, hence, the separation, can be controlled.

The pressure at which the reaction of the present process is conducted is not critical and may be varied from 0.01 to 10 atmospheres, preferably 1 to 2 atmospheres. It is most preferred to operate at atmospheric pressure.

Preferably the contents of the reaction mixture are agitated to maintain a well mixed slurry of the silicon particles and methanol in the solvent.

Whereas, the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

Equipment

The experiments include the following components: a MeOH feed system, the 6" diameter mechanically agitator reactor, a partial condenser and an entrainment separator, a reactor condenser, a distillation column feed system, a distillation column, a lites condenser and reflux splitter, a lites recycle system, and a product collection system.

The purpose of the methanol feed system is to provide vaporized make-up methanol to the reactor. The methanol feed system is comprised of a 1000 ml methanol feed tank, a FMI laboratory feed pump, a ⅛" diameter × 10 foot long vaporizer, a 1-gallon vaporizer hot oil bath.

Before this system is operated, the hot oil batch is heated to 150° C. and maintained there by a temperature controller. This insures a complete vaporization of the methanol. Heat tracing on the line from the vaporizer to the reactor is turned on to assure that no condensation occurs. The FMI pump is set to provide the desired MeOH flow to the vaporizer. Liquid MeOH is periodically added to the charge tank to assure that the flow is not interrupted.

The reactor is a 6" ID × 13" tall, rounded bottom, stirred vessel. Four 90° spaced, 0.5" wide baffles are supported from the reactor head. Agitation is provided by a single flat blade turbine 2.5" diameter having six blades which are 0.31" wide. This agitator is mounted at the axis of the reactor and is 2" above the bottom. Power is supplied by a variable speed air motor and RPM is measured by a magnetic tachometer. Vaporized methanol is introduced below the agitator through a single tube sparger which points downward in order to avoid plugging. Heating is provided by an electric heating mantle which is regulated by a temperature controller which monitors slurry temperature.

Prior to feeding methanol, the reactor is heated to 250° C. and the first step in operating the reactor is to charge the desired quantity of THERMINOL TM, Silicon and $Cu(OH)_2$ to the reactor. Before the silicon and $Cu(OH)_2$ were added, the agitator is started (usually at 700 RPM) to assure good solids suspension. A small $N_2$ purge is used on the sparge to avoid solids plugging. After this step and prior to feeding methanol, the reactor is heated to the reaction temperature and maintained there; then methanol feed is started and the $N_2$ purge is turned off.

After a run, the reactor is cooled and usually the flanged head is removed. The spent slurry is removed and the reactor is cleaned for the next run.

The gaseous reactor product flows to a partial condenser located on the top of the reactor. The purpose of this unit is to condense vaporized THERMINOL TM and return it to the reactor.

Example 1

In this example, the reactor temperature was 250° C. Reactor product was condensed prior to entering the distillation column. Solvent, silicon and copper addition was batchwise while methanol addition was continuous.

For start up, 150 cm³ of methanol was placed in the crude surge tank. This material was circulated through the reactor and the distillation column was not operated. After 2 hours, the make up MeOH flow to the reactor was started and the distillation column placed on stream.

The detailed data are presented in Table 1. These results can be summarized as follows:

| | |
|---|---|
| Run Time = | 21 hours |
| Average Make Up MeOH = | 3.0 grams/min |
| Average Selectivity, TMS/TTMS = | 9 |
| Silicon Utilization = | 81.5% |

Example 2

The detailed data are presented in Table 2. The results can be summarized as follows:

| | |
|---|---|
| Run Time | = 15.5 hours |
| Average Make Up MeOH | = 4.2 grams/min |
| Average Selectivity, TMS/TTMS | = 10.9 |

-continued

| Silicon Utilization | = 92% |

In this example, the reactor temperature was 250° C. Reactor product was condensed prior to entering the distillation column. Solvent, silicon and copper addition were batchwise while methanol addition was continuous.

During start up, only the reactor was operated. For the first two hours, make-up methanol flow to the reactor was about 1 gram/minute. Then the make up methanol flow was increased to about 5 grams/minute and the distillation column was turned on.

Example 3

The detailed data from this run are presented in Table III. These results can be summarized as follows:

| | |
|---|---|
| Run Time | = 17.5 hours |
| Reactor Temperature | = 250° C. |
| Average Make Up MeOH | = 3.3 grams/min |
| Average Selectivity, TMS/TTMS | = 13.0 |
| Silicon Utilization | = 92.8% |

In this example, the reactor was close-coupled to the distillation column. In other words, the gaseous reactor product was fed directly into the column.

During start up, the reactor and the distillation column were both operated. For the first 2 hours the make up methanol pump was set at about 1 gram/minute. Then the methanol flowrate was increased to about 4 grams/minute. Toward the end of the run, when silicon reactivity was largely depleted, make up methanol was again decreased in order to obtain good MeOH conversion.

Example 4

The detailed data from this run are presented in Table 4. These results are summarized as follows:

| | |
|---|---|
| Run Time | = 20 hours |
| Reactor Temperature | = 220° C. |
| Average Make Up MeOH | = 2.9 grams/min |
| Average Selectivity, TMS/TTMS | = 8.4 |
| Silicon Utilization | = 85.4% |

The operating sequence used in this example is analogous to Example 3, except that the reaction temperature was 220° C.

Example 5

The detailed data from this run are presented in Table 5. These results can be summarized as follows:

| | |
|---|---|
| Run Time | = 20.25 hours |
| Reactor Temperature | = 280° C. |
| Average Make Up MeOH | = 2.7 grams/min |
| Average Selectivity, TMS/TTMS | = 21.0 |
| Silicon Utilization | = 67.4% |

The operating sequence used in this example is analogous to Example 3, except that the reaction temperature is 280° C.

Example 6

The detailed data from this run are presented in Table 6. These results can be summarized as follows:

| | |
|---|---|
| Run Time | = 58 hours |
| Reactor Temperature | = 250° C. |
| Average Make Up MeOH | = 3.0 grams/min |
| Average Selectivity, TMS/TTMS | = 12.3 |
| Silicon Utilization | = 91.1% |

In this example, the reactor was close-coupled to the distillation column and the first 15 hours of operation were analogous to Example 3.

However, after about 700 grams of silicon metal had been consumed, the reaction was halted and the reactor was cooled down; then 700 grams of make-up silicon were added along with 4.62 grams of catalyst then the reactor was heated to 250° C. and the reaction was restarted. This sequence was repeated a total of three times.

| Elapsed Time, Hr. | Silicon Charge, grams |
|---|---|
| 0 | 1070 |
| 15.5 | 700 |
| 30.0 | 700 |
| 44.0 | 626 |

After the last silicon charge, the reaction was allowed to continue until silicon reactivity became too low to operate.

TABLE 1

| Elapsed Time, Hour | Reactor Outlet, g/min | MeOH Make-Up g/min | Recycle g/min | Column Boil Up g/min | Reactor Product, wt % | | | | Lites, wt % | | | Heavies, wt % | | |
|---|---|---|---|---|---|---|---|---|---|---|---|---|---|---|
| | | | | | MeOH | DMS | TMS | TTMS | MeOH | DMS | TMS | MeOH | TMS | TTMS |
| 1 | 5.09 | — | * | 17.6 | 12.6 | 0.9 | 82.2 | 2.3 | — | — | — | — | — | — |
| 2 | 6.33 | — | * | 17.6 | 0.4 | 1.4 | 77.2 | 19.4 | — | — | — | — | — | — |
| 3 | 5.60 | 2.50 | 1.17 | 17.6 | 9.8 | 1.7 | 80.1 | 7.3 | — | — | — | — | — | — |
| 4 | 5.24 | 3.16 | 1.17 | 17.6 | 5.9 | 4.1 | 84.3 | 4.4 | 20.1 | 7.1 | 68.8 | 0.5 | 64.8 | 32.6 |
| 5 | 4.6 | 3.42 | 1.04 | 17.6 | 4.2 | 5.1 | 84.6 | 4.7 | — | — | — | — | — | — |
| 5.3 | 3.73 | 3.42 | 0 | 17.6 | 3.9 | 2.8 | 88.8 | 3.1 | — | — | — | — | — | — |
| 6 | 4.44 | 3.36 | 0.77 | 17.6 | 3.9 | 5.0 | 85.8 | 4.0 | 18.8 | 20.1 | 55.2 | 0.05 | 84.8 | 13.6 |
| 7 | 4.80 | 3.03 | 0.77 | 17.6 | 3.3 | 5.6 | 85.1 | 4.5 | 14.2 | 21.5 | 58.6 | 0.07 | 91.3 | 7.3 |
| 8 | 3.77 | 3.03 | 0.66 | 17.6 | 4.0 | 5.4 | 85.9 | 3.1 | — | — | — | — | — | — |
| 9 | 4.12 | 2.8 | 0.66 | 17.6 | 4.3 | 5.4 | 85.1 | 3.6 | 17.0 | 22.8 | 57.5 | 0.04 | 90.4 | 7.2 |
| 10 | 4.11 | 2.9 | 0.66 | 17.6 | 4.3 | 5.6 | 83.7 | 4.8 | — | — | — | — | — | — |
| 11 | 4.53 | 2.9 | 0.66 | 17.6 | 4.4 | 5.3 | 84.1 | 4.8 | 22.5 | 25.4 | 48.5 | 0.05 | 92.9 | 5.6 |
| 11.3 | 3.87 | 2.9 | 0 | 17.6 | 4.6 | 1.9 | 87.9 | 4.2 | — | — | — | — | — | — |
| 12 | 3.88 | 2.71 | 0.66 | 17.6 | 5.3 | 5.4 | 82.1 | 5.6 | — | — | — | — | — | — |
| 13 | 4.76 | 2.9 | 0.66 | 17.6 | 5.3 | 4.1 | 84.1 | 5.0 | 23.6 | 19.4 | 53.1 | 0.06 | 92.6 | 6.0 |
| 14 | 3.83 | 2.9 | 0.66 | 17.6 | 5.5 | 4.6 | 81.9 | 5.4 | 25.1 | 17.8 | 53.0 | 0.09 | 91.9 | 6.7 |

TABLE 1-continued

| Elapsed Time, Hour | Reactor Outlet, g/min | MeOH Make-Up g/min | Recycle g/min | Column Boil Up g/min | Reactor Product, wt % | | | | Lites, wt % | | | Heavies, wt % | | |
|---|---|---|---|---|---|---|---|---|---|---|---|---|---|---|
| | | | | | MeOH | DMS | TMS | TTMS | MeOH | DMS | TMS | MeOH | TMS | TTMS |
| 15 | 4.41 | 3.03 | 0.66 | 17.6 | 9.1 | 3.7 | 81.2 | 4.2 | — | — | — | — | — | — |
| 16 | 4.68 | 3.09 | 1.26 | 17.6 | 9.8 | 4.2 | 78.0 | 6.2 | 30.0 | 14.6 | 52.7 | 0.04 | 87.2 | 10.4 |
| 16.5 | 4.0 | 3.09 | 0 | 17.6 | 9.8 | 1.2 | 83.3 | 4.2 | — | — | — | — | — | — |
| 17 | 4.57 | 3.09 | 1.26 | 17.6 | 11.6 | 4.6 | 74.2 | 8.0 | — | — | — | — | — | — |
| 18 | 5.26 | 3.03 | 1.26 | 17.6 | 11.9 | 3.7 | 76.0 | 7.3 | 39.8 | 11.9 | 46.1 | 0.03 | 89.4 | 9.0 |
| 19 | 5.26 | 2.77 | 1.74 | 17.6 | 16.8 | 4.3 | 71.3 | 6.1 | — | — | — | — | — | — |
| 20 | 5.49 | 2.90 | 1.74 | 17.6 | 20.8 | 3.8 | 68.9 | 5.3 | 40.8 | 8.6 | 48.5 | 0.05 | 88.2 | 9.9 |
| 21 | 5.43 | 3.16 | 1.74 | 17.6 | 30.9 | 3.1 | 59.6 | 5.3 | 41.9 | 5.9 | 49.3 | 0.2 | 88.1 | 10.1 |
| System Drain | | | | | 13.6 | 1.0 | 75.9 | 8.3 | | | | | | |

*Not Measured

TABLE 2

| Elapsed Time, Hour | Reactor Outlet, g/min | MeOH Make-Up g/min | Recycle g/min | Column Boil Up g/min | Reactor Product, wt % | | | | Lites, wt % | | | Heavies, wt % | | |
|---|---|---|---|---|---|---|---|---|---|---|---|---|---|---|
| | | | | | MeOH | DMS | TMS | TTMS | MeOH | DMS | TMS | MeOH | TMS | TTMS |
| — | Starting | Crude | | 200 gms | 0.9 | 0.5 | 58.5 | 38.7 | — | — | — | — | — | — |
| 1 | * | 1.05 | 0 | 15.5 | 41.4 | 1.0 | 52.8 | 1.0 | — | — | — | — | — | — |
| 2 | 1.36 | 1.05 | 4.86 | 15.5 | 11.6 | 1.7 | 84.9 | 0.6 | — | — | — | — | — | — |
| 3.5 | 11.2 | 5.8 | 3.74 | 15.5 | 12.3 | 3.0 | 80.9 | 2.5 | 42.1 | 4.6 | 51.4 | 7.8 | 61.5 | 26.5 |
| 3.6 | 6.01 | 5.0 | 0 | 15.5 | 5.5 | 2.7 | 87.2 | 3.2 | — | — | — | — | — | — |
| 5 | 10.3 | 5.0 | 3.74 | 15.5 | 6.3 | 5.3 | 83.9 | 3.2 | 18.5 | 11.5 | 66.9 | 0.2 | 90.3 | 7.6 |
| 5.1 | 6.06 | 5.0 | 0 | 15.5 | 5.5 | 2.7 | 87.2 | 3.2 | — | — | — | — | — | — |
| 6.5 | 10.5 | 4.74 | 3.74 | 15.5 | 5.4 | 6.3 | 82.2 | 4.3 | 14.5 | 14.5 | 65.9 | 0.04 | 92.7 | 5.5 |
| 8 | 10.0 | 5.70 | 3.96 | 15.5 | 6.7 | 7.0 | 80.1 | 4.1 | 20.6 | 19.3 | 57.3 | 0.05 | 89.2 | 8.0 |
| 8.1 | 6.06 | 4.74 | 0 | 15.5 | 7.3 | 2.0 | 85.5 | 3.7 | — | — | — | — | — | — |
| 9.5 | 9.52 | 5.4 | 2.47 | 15.5 | 10.5 | 7.2 | 76.4 | 4.1 | 32.5 | 22.2 | 42.5 | 0.05 | 90.7 | 6.8 |
| 9.6 | 6.28 | 5.4 | 0 | 15.5 | 9.9 | 1.8 | 83.1 | 3.6 | — | — | — | — | — | — |
| 11 | 9.33 | 5.37 | 2.47 | 15.5 | 16.9 | 5.2 | 72.0 | 4.2 | 37.6 | 13.7 | 45.8 | 0.03 | 91.4 | 6.4 |
| 11.1 | 6.19 | 5.13 | 0 | 15.5 | 16.5 | 1.2 | 77.0 | 3.7 | — | — | — | — | — | — |
| 12.1 | 13.2 | 5.53 | 4.16 | 15.5 | 29.5 | 4.3 | 61.9 | 3.0 | 6.6 | — | 49.5 | 0.7 | 90.9 | 6.4 |
| 12.4 | 5.9 | 5.0 | 0 | 15.5 | 27.5 | 0.8 | 67.4 | 3.1 | — | — | — | — | — | — |
| 13 | 7.26 | 0 | 6.52 | 15.5 | 9.6 | 7.5 | 70.9 | 9.8 | 20.9 | 9.1 | 65.9 | 0.1 | 87.0 | 10.4 |
| 14 | 5.78 | 5.4 | 0 | 15.5 | 52.5 | | 43.4 | 2.9 | — | — | — | — | — | — |
| 15 | 7.93 | 5.4 | * | 15.5 | 29.8 | 3.5 | 60.0 | 5.2 | 43.2 | 3.3 | 52.5 | — | — | — |
| 15.5 | * | 0 | * | 15.5 | 33.2 | 4.8 | 55.7 | 4.9 | — | — | — | 1.2 | 57.0 | 38.3 |
| System Drain | | | | | 15.4 | 1.7 | 64.4 | 16.8 | | | | | | |

TABLE 3

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 3 | 3.7 | 2.85 | 12.7 | — | — | — | 1.8 | 81.1 | 10.7 |
| 4 | 4.5 | 1.55 | 12.7 | 24.8 | 12.3 | 60.9 | 0.4 | 90.1 | 6.7 |
| 5 | 4.5 | 0.8 | 12.7 | — | — | — | 0.07 | 93.6 | 4.8 |
| 6 | 4.4 | 0.8 | 12.7 | 28.3 | 24.5 | 43.2 | 0.3 | 94.3 | 4.0 |
| 7 | 4.2 | 0.8 | 12.7 | 25.9 | 23.7 | 46.5 | 0.05 | 94.9 | 3.8 |
| 8 | 4.4 | 0.8 | 12.7 | 24.0 | 15.8 | 57.0 | 0.05 | 93.7 | 5.0 |
| 9 | 4.4 | 0.8 | 12.7 | — | — | — | 0.05 | 92.6 | 5.9 |
| 10 | ~4.4 | 0.8 | 12.7 | — | — | — | 0.07 | 93.2 | 5.4 |
| 11.5 | 4.4 | 0.8 | 12.7 | 41.6 | 7.3 | 48.3 | 0.2 | 92.0 | 6.3 |
| 12.5 | 4.2 | 1.85 | 12.7 | 42.6 | 3.7 | 51.0 | 0.7 | 91.2 | 6.5 |
| 13.5 | 4.4 | 1.85 | 12.7 | — | — | — | 0.3 | 91.7 | 6.9 |
| 14.5 | 4.6 | 5.0 | 12.7 | 43.7 | 1.1 | 53.2 | 1.4 | 90.5 | 7.0 |
| 15.5 | * | * | 12.7 | — | — | — | 1.4 | 86.0 | 10.9 |
| 16.5 | * | * | 12.7 | 44.0 | 0.6 | 54.0 | 1.0 | 83.1 | 14.0 |
| 17.5 | * | * | 12.7 | 44.2 | 0.5 | 54.3 | 8.0 | 77.2 | 13.1 |

*Variable

TABLE 4

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 3 | 3.03 | 2.4 | 12.7 | 41.2 | 1.7 | 54.4 | 1.7 | 83.2 | 9.7 |
| 4 | 2.63 | 1.85 | 12.7 | — | — | — | 0.09 | 86.3 | 10.5 |
| 5 | 3.29 | 1.85 | 12.7 | 26.3 | 3.0 | 69.1 | 0.04 | 89.3 | 8.6 |
| 6 | 3.16 | 0.95 | 12.7 | — | — | — | 0.05 | 90.1 | 8.3 |
| 7 | 3.29 | 0.95 | 12.7 | 40.6 | 7.7 | 48.6 | 0.05 | 91.5 | 7.2 |
| 8 | 3.42 | 0.95 | 12.7 | 28.5 | 7.0 | 62.9 | 0.05 | 86.1 | 10.0 |
| 9 | 3.16 | 0.95 | 12.7 | — | — | — | 0.04 | 89.7 | 8.0 |
| 10 | 3.29 | 0.95 | 12.7 | 39.0 | 9.7 | 49.5 | 0.04 | 90.7 | 7.6 |
| 11 | 3.29 | 0.95 | 12.7 | — | — | — | 0.02 | 90.7 | 7.8 |

TABLE 4-continued

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 12 | 3.16 | 0.95 | 12.7 | 40.6 | 9.0 | 47.4 | 0.04 | 90.9 | 8.0 |
| 13 | 3.29 | 0.95 | 12.7 | — | — | — | 0.2 | 90.6 | 8.2 |
| 14 | 3.29 | 0.95 | 12.7 | 41.2 | 7.6 | 50.3 | 0.04 | 89.6 | 8.9 |
| 15 | 3.29 | 0.95 | 12.7 | 42.3 | 4.3 | 49.6 | 0.06 | 86.2 | 11.2 |
| 16 | 3.29 | 3.95 | 12.7 | — | — | — | 0.5 | 86.8 | 10.9 |
| 17 | 3.29 | 4.4 | 12.7 | 43.5 | 1.4 | 53.6 | 0.6 | 84.0 | 12.9 |
| 18 | 2.63* | 4.4 | 12.7 | — | — | — | 0.6 | 82.8 | 14.8 |
| 19 | 2.2 | 4.4 | 12.7 | 43.4 | 1.0 | 54.5 | 0.06 | 83.0 | 15.1 |
| 20 | 2.0 | 5.6 | 12.7 | 44.0 | 0.8 | 54.0 | 0.9 | 82.5 | 14.8 |
| System Drain | — | — | — | — | — | — | 8.0 | 75.9 | 14.4 |

*Variable

TABLE 5

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 3 | 3.03 | 1.85 | 12.7 | 36.6 | 13.2 | 47.9 | 0.4 | 86.9 | 7.1 |
| 4 | 3.16 | 1.85 | 12.7 | — | — | — | 0.03 | 91.7 | 4.9 |
| 5 | 3.16 | 1.85 | 12.7 | 17.4 | 11.7 | 69.1 | 0.04 | 94.2 | 3.5 |
| 6 | 3.16 | 1.85 | 12.7 | 23.4 | 16.2 | 58.0 | 0.05 | 94.9 | 3.0 |
| 7 | 3.42 | 1.85 | 12.7 | 19.7 | 5.1 | 73.1 | 0.04 | 93.1 | 3.1 |
| 8 | 3.16 | 1.85 | 12.7 | — | — | — | 0.05 | 93.8 | 3.5 |
| 9 | 3.42 | 1.85 | 12.7 | 33.4 | 18.7 | 46.0 | 0.05 | 94.6 | 3.2 |
| 10 | 2.90 | 1.85 | 12.7 | — | — | — | 0.05 | 95.1 | 3.1 |
| 11 | 3.03 | 1.85 | 12.7 | 32.4° | 10.0 | 55.4 | 0.05 | 95.4 | 3.2 |
| 12 | 3.03 | 1.85 | 12.7 | — | — | — | 0.04 | 95.5 | 3.1 |
| 12.75 | 3.16 | 1.85 | 12.7 | 37.2 | 13.0 | 47.3 | 0.04 | 95.3 | 3.1 |
| 13.75 | 3.16 | 1.85 | 12.7 | 39.5 | 7.8 | 51.0 | 0.9 | 90.6 | 4.6 |
| 14.75 | 3.16 | 1.85 | 12.7 | — | — | — | 0.09 | 92.8 | 4.3 |
| 15.75 | 3.16 | 1.85 | 12.7 | 39.8 | 9.9 | 48.3 | 0.1 | 93.9 | 3.7 |
| 16.75 | 3.03 | 4.7* | 12.7 | — | — | — | 1.0 | 92.7 | 3.9 |
| 17.75 | * | * | 12.7 | 6.2 | 3.9 | 88.7 | 0.1 | 92.4 | 4.4 |
| 18.75 | 2.0 | 3.3 | 12.7 | — | — | — | 0.08 | 91.2 | 5.9 |
| 20.25 | 2.0 | 5.6* | 12.7 | 42.2 | 4.6 | 51.8 | 1.9 | 88.8 | 6.8 |
| System Drain | — | — | — | — | — | — | 4.4 | 85.7 | 7.2 |

TABLE 6

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 3 | 3.03 | 4.0 | 12.7 | 41.1 | 6.8 | 50.2 | 1.4 | 92.0 | 4.3 |
| 4 | 3.03 | 1.85 | 12.7 | — | — | — | 0.1 | 92.2 | 5.8 |
| 5 | 3.03 | 1.4 | 12.7 | 8.9 | 17.9 | 71.7 | 0.03 | 92.6 | 5.4 |
| 6 | 3.42 | 0.95 | 12.7 | 19.2 | 19.8 | 57.4 | 0.03 | 91.2 | 5.0 |
| 7 | 3.29 | 0.95 | 12.7 | — | — | — | 0.04 | 92.5 | 4.9 |
| 8 | 3.16 | 0.95 | 12.7 | 21.2 | 26.5 | 49.8 | 0.03 | 93.1 | 4.6 |
| 9.1 | 3.28 | 0.95 | 12.7 | — | — | — | 0.03 | 93.6 | 4.8 |
| 10 | 3.16 | 0.95 | 12.7 | 21.1 | 21.5 | 55.2 | 0.03 | 93.3 | 5.1 |
| 11 | 3.16 | 0.95 | 12.7 | 17.7 | 18.3 | 61.3 | 0.03 | 92.7 | 5.4 |
| 12 | 3.16 | 0.95 | 12.7 | 23.8 | 17.2 | 55.9 | 0.04 | 89.5 | 6.0 |
| 13 | 3.29 | 0.95 | 12.7 | — | — | — | 0.05 | 91.6 | 5.6 |
| 14 | 3.16 | 0.95 | 12.7 | 37.9 | 14.1 | 45.6 | 0.04 | 92.6 | 5.6 |
| 15 | 3.29 | 0.95 | 12.7 | — | — | — | 0.03 | 92.9 | 5.6 |
| 15.5 | 3.16 | 0.95 | 12.7 | 39.9 | 11.6 | 45.6 | 0.03 | 92.3 | 5.7 |
| 16.5 | 2.77 | 0.95 | 12.7 | 36.7 | 17.5 | 41.5 | 0.1 | 87.8 | 7.2 |
| 17.5 | 3.03 | 0.95 | 12.7 | — | — | — | 0.1 | 90.5 | 6.4 |
| 18.5 | 3.16 | 1.85 | 12.7 | 13.4 | 10.9 | 73.5 | 0.09 | 91.3 | 6.5 |
| 19.5 | 3.16 | 1.40 | 12.7 | — | — | — | 0.04 | 91.6 | 6.4 |
| 20.5 | ~3.16 | 1.40 | 12.7 | 24.9 | 11.9 | 60.4 | 0.04 | 92.1 | 5.9 |
| 21.5 | 3.03 | 1.40 | 12.7 | — | — | — | 0.04 | 92.3 | 6.2 |
| 22.5 | 3.16 | 1.40 | 12.7 | 27.6 | 14.4 | 44.4 | 0.03 | 92.6 | 6.1 |
| 23.5 | 3.29 | 1.40 | 12.7 | 37.1 | 13.1 | 45.7 | 0.05 | 89.3 | 6.8 |
| 24.5 | 3.16 | 1.40 | 12.7 | — | — | — | 0.04 | 90.8 | 6.8 |
| 25.5 | 3.29 | 1.85 | 12.7 | 24.2 | 13.3 | 59.7 | 0.2 | 90.3 | 7.5 |
| 26.5 | 3.29 | 0.95 | 12.7 | — | — | — | 0.04 | 90.3 | 7.5 |
| 27.5 | 3.03 | 0.95 | 12.7 | 40.4 | 11.2 | 44.8 | 0.2 | 91.5 | 6.7 |
| 28.5 | 3.16 | 0.95 | 12.7 | — | — | — | 0.04 | 91.2 | 7.4 |
| 30 | 3.07 | 0.95 | 12.7 | 41.6 | 6.9 | 49.1 | 0.04 | 91.2 | 7.4 |
| 31 | ~1 g/min | 5.3 | 12.7 | 42.0 | 5.1 | 49.5 | 1.2 | 77.0 | 7.0 |
| 32 | ~2.1* | 4.0 | 12.7 | — | — | — | 1.6 | 81.7 | 7.1 |
| 33 | ~3.0 | 1.85 | 12.7 | 38.9 | 12.9 | 43.5 | 0.1 | 87.7 | 6.4 |
| 34 | 3.29 | 2.6 | 12.7 | — | — | — | 0.3 | 92.0 | 5.3 |
| 35 | ~3 | 1.4 | 12.7 | 36.5 | 8.8 | 51.7 | 0.04 | 92.0 | 6.0 |

TABLE 6-continued

| Elapsed Time, Hr. | MeOH Make-Up g/min | Recycle g/min | Column Boil Up g/min | Lites, wt % | | | Heavies, wt % | | |
|---|---|---|---|---|---|---|---|---|---|
| | | | | MeOH | DMS | TMS | MeOH | TMS | TTMS |
| 36 | 3.29 | * | 12.7 | — | — | — | 0.03 | 91.4 | 6.9 |
| 37 | 3.16 | * | 12.7 | 28.2 | 7.1 | 61.7 | 0.04 | 91.2 | 7.4 |
| 38 | 3.03 | * | 12.7 | 38.3 | 4.9 | 54.8 | 0.04 | 80.9 | 6.5 |
| 39 | 3.16 | * | 12.7 | — | — | — | 0.04 | 85.5 | 5.8 |
| 40 | 3.29 | 0.78 | 12.7 | 42.1 | 5.9 | 49.9 | 0.03 | 89.0 | 6.7 |
| 41 | 3.29 | 0.78 | 12.7 | — | — | — | 0.03 | 89.7 | 8.2 |
| 42 | 3.16 | 0.78 | 12.7 | 40.2 | 5.6 | 52.1 | 0.04 | 90.0 | 8.3 |
| 43 | 3.29 | 0.78 | 12.7 | — | — | — | 0.03 | 90.5 | 8.1 |
| 44 | 3.29 | 1.6 | 12.7 | 42.9 | 3.4 | 52.0 | 0.02 | 90.3 | 8.4 |
| 45 | 3.16 | 1.4 | 12.7 | 42.0 | 3.4 | 51.9 | 0.02 | 73.9 | 10.0 |
| 46 | 2.63* | 2.6 | 12.7 | — | — | — | 0.7 | 81.2 | 9.1 |
| 47 | 3.29 | 6.5 | 12.7 | 40.7 | 6.9 | 49.8 | 1.7 | 87.9 | 6.6 |
| 48 | 3.42 | 6.5 | 12.7 | — | — | — | 0.06 | 91.9 | 5.4 |
| 49 | 3.03 | 2.6 | 12.7 | 34.6 | 8.1 | 54.5 | 0.03 | 92.9 | 5.2 |
| 50 | 3.29 | 1.8 | 12.7 | — | — | — | 0.03 | 91.0 | 7.3 |
| 51 | 3.42 | 1.8 | 12.7 | 28.8 | 5.0 | 64.8 | 0.07 | 90.0 | 8.5 |
| 52 | 3.29 | 1.8 | 12.7 | 26.9 | 4.3 | 67.0 | 0.05 | 87.6 | 8.8 |
| 53 | 3.29 | 1.8 | 12.7 | — | — | — | 0.05 | 88.0 | 9.4 |
| 54 | 3.42 | 1.8 | 12.7 | 36.5 | 1.9 | 60.0 | 0.04 | 88.5 | 9.8 |
| 55 | 3.29 | 1.8 | 12.7 | — | — | — | 0.09 | 88.3 | 10.1 |
| 56 | 2.90* | 4.0* | 12.7 | 43.2 | 2.1 | 53.1 | 2.0 | 84.8 | 11.6 |
| 57 | 2.1 | 4.0 | 12.7 | — | — | — | 0.09 | 83.9 | 14.2 |
| 58 | 1.6* | 4.0* | 12.7 | 42.7 | 0.9 | 55.0 | 0.08 | 79.9 | 17.3 |
| System Drain | — | — | — | — | — | — | 0.05 | 78.2 | 16.5 |

*Variable

The examples illustrate conditions under which the process of the present invention can be advantageously operated. Table 7 summarizes how the parameters were varied in the examples and the results that were obtained. Examples 1 to 3 demonstrate that close-coupling the reactor and column improves selectivity. Examples 3 to 6 demonstrate that higher reaction temperatures improve selectivity; however, in Example 5, % silicon conversion was low, but product selectivity was high. Examples 4 and 6 overall demonstrate acceptable selectivity and % silicon conversion.

TABLE 7

| | | Condition | | | | Results | |
|---|---|---|---|---|---|---|---|
| Example | Start Up Mode | Reactor-Column Coupling* (during operation) | Reactor Temperature | Feed Rate gm/min | Silicon/Cu added During Run | % Si Conversion | Product (Heavies) Selectivity TMS/(TIMS) |
| 1 | MeOH Recycled thru reactor Column off | Decoupled | 250° C. | 3.0 | No | 81.5 | 9 |
| 2 | MeOH Recycled thru reactor Column off | Decoupled | 250° C. | 4.2 | No | 92 | 10.9 |
| 3 | Reactor & Column started up together | Close-coupled | 250° C. | 3.3 | No | 92 | 13.0 |
| 4 | Reactor & Column started up together | Close-coupled | 220° C. | 2.9 | No | 85.4 | 8.4 |
| 5 | Reactor & Column started up together | Close-coupled | 280° C. | 2.7 | No | 67.4 | 21.0 |
| 6 | Reactor & Column started up together | Close-coupled | 250° C. | 3.0 | Yes | 91.1 | 12.3 |

*Decoupled: reactor product condensed, then fed to column
Close-coupled: reactor product directly fed as gas to column That which is claimed is:

1. A process for producing trimethoxysilane comprising:
   (1) introducing methanol into a reactor containing a slurry of silicon metal and a catalytically effective amount of a copper catalyst which reactor is maintained at a temperature of at least 180° C.;
   (2) reacting the methanol and silicon metal while maintaining the percent methanol conversion at least 60% to form a reactor product containing essentially trimethoxysilane-methanol azeotrope and trimethoxysilane;
   (3) introducing the reactor product immediately to a column wherein the reactor product is distilled to form (i) a lites stream containing predominantly the trimethoxysilane-methanol azeotrope and (ii) a heavies stream containing predominantly trimethoxysilane;
   (4) recycling said lites stream from the column to the reactor; and
   (5) removing said heavies stream from the column.

2. A process according to claim 1 wherein the temperature in the reactor ranges from about 200° C. to 280° C.

3. A process according to claim 2, wherein the temperature ranges from about 240° C. to 280° C.

4. A process according to claim 1 wherein the reactor contains at least one inert solvent.

5. A process according to claim 4 wherein the solvent is selected from the group consisting of paraffinic hydrocarbon, polyalkylated aromatic hydrocarbon and mixtures thereof.

6. A process according to claim 5 wherein the solvent is a polyalkylated aromatic hydrocarbon.

7. A process according to claim 1 wherein the silicon metal is in particulate form.

8. A process according to claim 1 wherein the catalyst is a copper catalyst selected from the group consisting of cupric oxide, cuprous oxide, cupric chloride, cuprous chloride, copper hydroxide and mixtures thereof.

9. A process according to claim 8 wherein the catalyst is copper hydroxide.

10. A process according to claim 1 wherein the catalyst is stabilized copper (II) hydroxide.

11. A process according to claim 5 wherein the catalyst is stabilized copper (II) hydroxide.

12. A process according to claim 8 wherein the effective amount of copper catalyst ranges from about 0.1 to about 2.6 parts by weight per 100 parts by weight of silicon metal.

13. A process according to claim 12 wherein the effective amount of copper catalyst ranges from about 0.1 to 0.7 parts by weight per 100 parts by weight of silicon metal.

14. A process according to claim 1 wherein the reactor is a fluidized bed reactor.

15. A process according to claim 1 wherein the reactor is a fixed bed reactor.

16. A process according to claim 1 wherein the reactor is a moving bed reactor.

17. A process according to claim 3 wherein the reactor is a slurry reactor.

18. A process according to claim 3 wherein the reactor is a mechanically agitated tank.

19. A process according to claim 3 wherein the reactor is a trickle bed.

20. A process according to claim 1 wherein the reactor consists of at least two reactors.

21. A process according to claim 1 wherein the column is a packed distillation column.

22. A process according to claim 1 wherein the column is a multi-stage distillation column.

23. A process according to claim 1 wherein the methanol is introduced to the reactor as liquid.

24. A process according to claim 1 wherein the methanol is introduced to the reactor as a gas.

25. A process according to claim 1 wherein the % methanol conversion per pass ranges from about 70 to about 85 percent.

26. A process according to claim 1 wherein the amount of methanol feeding into the reactor is controlled by monitoring the amount of lites stream recycled to the reactor.

27. A process according to claim 1 wherein the amount of methanol feeding into the reactor is controlled by monitoring the level of unreacted methanol in the reactor product.

28. A process according to claim 1 wherein the amount of methanol feeding into the reactor is controlled by monitoring the temperature at points in the distillation column.

29. A process according to claim 1 wherein the bottoms stream is fed to a second distillation column.

30. A process according to claim 1 wherein the reacting and mixing takes place at atmospheric pressure.

31. A process according to claim 5 wherein the solvent is present in an amount ranging from one part of solvent per two parts of silicon metal (1:2) to four parts of solvent per one part of silicon metal (4:1).

32. A process according to claim 28 wherein the solvent is present in an amount ranging from 1:1 to 1:2 parts of solvent to silicon.

33. A process according to claim 1 wherein the reactor product fed to a distillation column is substantially gaseous.

34. A process according to claim 1 wherein the percent methanol conversion is maintained by a temperature control means on the distillation column.

35. A process according to claim 1 wherein the percent methanol conversion is maintained by flow control means of the recycle of the azeotrope.

36. A process according to claim 1 wherein the percent methanol conversion is maintained by a temperature control means on the column and a flow control means of the recycle of the azeotrope.

37. A process for producing trimethoxysilane comprising:
  (1) introducing gaseous methanol into a reactor containing a slurry of silicon metal, a catalytically effective amount of stabilized copper (II) hydroxide catalyst, and a polyalkylated aromatic hydrocarbon inert solvent which reactor is maintained at a temperature ranging from about 240° C. to 280° C.;
  (2) reacting the methanol and silicon metal while maintaining the percent methanol conversion per pass at least 60% to form a reactor product containing essentially trimethoxysilane-methanol azeotrope and trimethoxysilane;
  (3) introducing the reactor product immediately to a distillation column wherein the reactor product is distilled to form (i) a lites stream containing predominantly the trimethoxysilane-methanol azeotrope and (ii) a heavies stream containing predominantly trimethoxysilane;
  (4) recycling a portion of said lites stream to the reactor and wherein said lites stream is substantially in gaseous form; and
  (5) removing said heavies stream.

38. A process according to claim 37 wherein the % methanol conversion is at least 80% per pass.

* * * * *